(12) United States Patent
Truschel

(10) Patent No.: US 6,360,741 B2
(45) Date of Patent: *Mar. 26, 2002

(54) PRESSURE SUPPORT SYSTEM WITH A LOW LEAK ALARM AND METHOD OF USING SAME

(75) Inventor: William A. Truschel, Monroeville, PA (US)

(73) Assignee: Respironics, Inc., Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/436,858

(22) Filed: Nov. 9, 1999

Related U.S. Application Data

(60) Provisional application No. 60/109,770, filed on Nov. 25, 1998.

(51) Int. Cl.[7] ............................................. A61M 16/00
(52) U.S. Cl. .......................... 128/202.22; 128/204.23; 128/204.21; 128/205.23
(58) Field of Search ....................... 128/202.22, 204.18, 128/204.21, 204.23, 205.23, 205.25, 207.13

(56) References Cited

U.S. PATENT DOCUMENTS

| | | | | |
|---|---|---|---|---|
| 4,773,411 A | * | 9/1988 | Downs | 128/204.18 |
| 4,803,471 A | * | 2/1989 | Rowland | 340/626 |
| 5,057,822 A | * | 10/1991 | Hoffman | 128/202.22 |
| 5,065,756 A | * | 11/1991 | Rapoport | 128/205.25 |
| 5,199,424 A | * | 4/1993 | Sullivan et al. | 128/204.18 |
| 5,335,654 A | * | 8/1994 | Rapoport | 128/204.23 |
| 5,535,738 A | * | 7/1996 | Estes et al. | 128/204.23 |
| 5,535,739 A | * | 7/1996 | Rapoport et al. | 128/204.21 |
| 5,540,219 A | * | 7/1996 | Mechlenburg et al. | 128/204.18 |
| 5,694,923 A | * | 12/1997 | Hete et al. | 128/204.23 |
| 5,865,173 A | * | 2/1999 | Froehlich | 128/204.21 |
| 6,105,575 A | * | 8/2000 | Estes et al. | 128/204.23 |

* cited by examiner

Primary Examiner—Aaron J. Lewis
(74) Attorney, Agent, or Firm—Michael W. Haas

(57) ABSTRACT

A pressure support system and method of using same that includes a pressure generator adapted to provide a gas flow, a conduit coupled to the pressure generator to deliver a gas flow to a patient, an interface device coupled to the conduit to communicate the gas flow to an airway of the patient. An exhaust vent that provides a flow of exhaust gas to atmosphere is provided in the conduit or the interface device. A flow sensor detects a rate at which gas flows in the conduit and provides a first output indicative thereof, and a pressure sensor detects a pressure of gas at the patient and provides a second output indicative thereof. A control system receives the first and second outputs and determines whether a current flow of exhaust gas passing through the exhaust vent is below an alarm threshold based on the first and second outputs and provides a third output indicative of this determination.

25 Claims, 3 Drawing Sheets

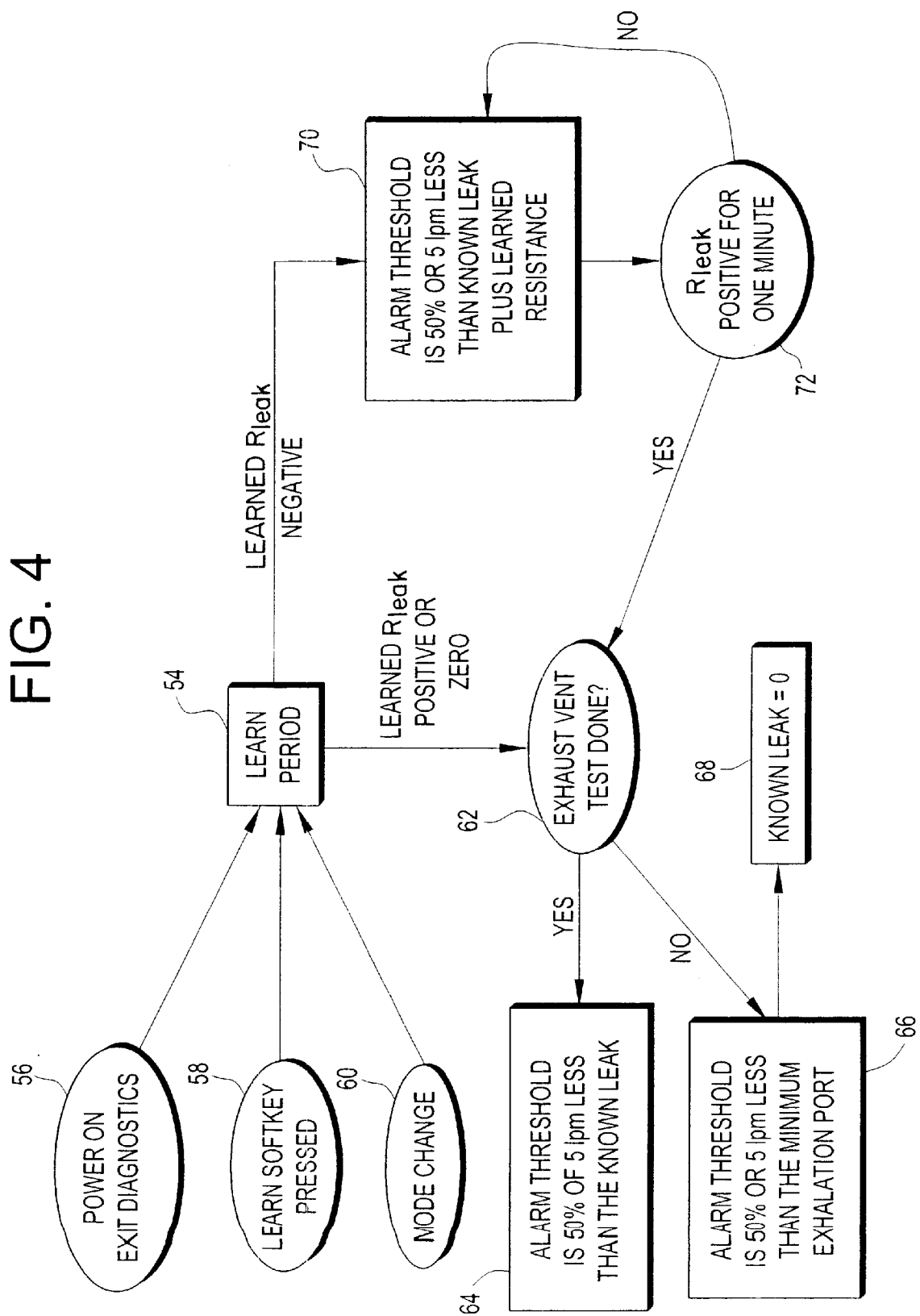

PRESSURE SUPPORT SYSTEM WITH A LOW LEAK ALARM AND METHOD OF USING SAME

CROSS-REFERENCE TO RELATED APPLICATIONS

This application claims priority under 35 U.S.C. §119(e) from U.S. provisional appliation No. 60/109,770 filed Nov. 25, 1998.

BACKGROUND OF THE INVENTION

1. Field of the Invention

The present invention pertains to a pressure support system that includes a low leak alarm and to a method of providing such an alarm, and, in particular, to a pressure support system, which provides positive pressure therapy to a patient via a single limb patient circuit, that includes an alarm indicating that the current system leak from the patient circuit via an exhaust port is below an acceptable level, which involves comparing a current system leak with an adaptive alarm threshold.

2. Description of the Related Art

Pressure support systems that provide a gas flow to an airway of a patient at an elevated pressure via a single limb patient circuit to treat a medical disorder are well known. For example, it is known to use a continuous positive airway pressure (CPAP) device to supply a constant positive pressure to the airway of a patient to treat obstructive sleep apnea (OSA). It is also known to provide a positive pressure therapy in which the pressure of gas delivered to the patient varies with the patient's breathing cycle or varies with the patient's effort to increase the comfort to the patient. It is further known to provide a positive pressure therapy in which the pressure provided to the patient changes based on the detected conditions of the patient, such as whether the patient is snoring or experiencing an apnea, hypopnea or upper airway resistance.

Conventional pressure support devices typically include a pressure generator, for example, a blower, piston or bellows, that creates a flow of breathing gas having a pressure greater than the ambient atmospheric pressure. A patient circuit delivers the elevated pressure breathing gas to the airway of the patient. Typically, the patient circuit includes a conduit, i.e., a single lumen, having one end coupled to the pressure generator and a patient interface device coupled to the other end of the conduit. The patient interface connects the conduit with the airway of the patient so that the elevated pressure gas flow is delivered to the airway of the patient. Examples of patient interface devices include a nasal mask, nasal and oral mask, full face mask, nasal cannula, oral mouthpiece, tracheal tube, endotracheal tube, or hood. A single limb patient circuit further includes an exhalation port, also referred to as an exhalation vent, exhaust port or exhaust vent, to allow expired gas from the patient to exhaust to atmosphere. Generally, the exhaust vent is located in the conduit near the patient interface and/or in the patient interface device itself.

A concern in a single limb pressure support device is that the exhalation port remains open during use so that a sufficient amount of expired gas exhausts from the system. Complete or partial blockage of the exhaust port can occur, for example, by a buildup of secretions from the patient in the exhaust port. Blockage can also occur as a result of an external item, such as the patient or the patient's bedding, covering the port. For example, a patient using the pressure support system at night to treat OSA might roll over during sleep so that the exhaust port is covered by the patient's sheets, pillow and/or mattress and cause a complete or partial blockage of one or more of the exhaust ports in the patient circuit.

Conventional pressure support device attempt to mitigate this concern by designing exhaust ports that are difficult to block. For example, multiple flow paths may be provided so that if one path becomes blocked, another path provides the necessary exhaust function. Also, routine maintenance, such as daily inspection and/or weekly cleaning, are recommended to ensure the integrity of the exhaust paths. These techniques, however, have several disadvantages. For example, they may not be sufficient to ensure the continuity of the exhaust paths at all times during the patient's therapy, are relatively time consuming, and place a significant burden on the user in requiring the user to perform the routine maintenance and to remember to perform the maintenance. In addition, these conventional techniques do nothing to warn the user that an exhaust port blockage has taken place at the time the blockage occurs.

SUMMARY OF THE INVENTION

Accordingly, it is an object of the present invention to provide a single limb pressure support device having an exhaust vent in the patient circuit and/or patient interface device and that does not suffer from the above disadvantages associated with conventional single limb pressure support devices. This object is achieved, according to one embodiment of the present invention, by providing a pressure support device that includes a pressure generator adapted to provide a gas flow, a conduit coupled to the pressure generator to deliver the gas flow to a patient, an interface device coupled to the conduit to communicate the gas flow to an airway of the patient, and an exhaust vent that provides a flow of exhaust gas to atmosphere from the conduit and/or the interface device. A first sensor detects the rate at which gas flows in the conduit, and a second sensor detects the pressure of gas at the patient. A control system receives the outputs from the first and second sensors and determines whether a current flow of exhaust gas passing through the exhaust vent is below an alarm threshold based on the first and second outputs and provides a third output indicative of this determination.

It is a further object of the present invention to allow the pressure support system to set the alarm threshold based on the specific conditions of that pressure support system, so that the alarm threshold is optimized for the current conditions of the pressure support system. This object is achieved, according to one embodiment of the present invention, by having the pressure support system enter a learn period in which at least one parameter associated with the pressure support system is monitored. This parameter, or a plurality of parameters, are used to set the alarm threshold. Thus, the present invention can set the alarm threshold taking into consideration the specific conditions of pressure support system, such as the introduction of a supplemental breathing gas, e.g. oxygen, into the system, and not produce a false alarm.

It is still another object of the present invention to provide a method of providing pressure support to a patient via a single limb circuit having an exhaust vent in that circuit and that does not suffer from the disadvantages associated with the above-described conventional single limb pressure support techniques. This object is achieved, according to one embodiment of the present invention, by providing a method of providing pressure support via a pressure support system, wherein the method includes the following steps: (1) providing a gas flow from a pressure generator to a patient via a conduit coupled to the pressure generator, wherein an interface device is also coupled to the conduit to communicate the gas flow from the conduit to an airway of the patient, and wherein an exhaust vent in disposed in the interface device or the conduit to communicate a flow of exhaust gas to atmosphere, (2) detecting a rate at which gas flows in the conduit, (3) detecting a pressure of gas at the patient, (4) determining whether a current rate at which exhaust gas passes through the exhaust vent is below an alarm threshold based on the detected gas flow and pressure, and (5) providing a third output indicative of a result of the determining step.

It is a still further object of the present to provide a method of setting the alarm threshold based on the conditions of the pressure support system so that the alarm threshold is optimized for the current conditions of the pressure support system. This object is achieved, according to one embodiment of the present invention, by monitoring the rate at which gas flows in the conduit and the pressure of gas at the patient during a learn period and setting the alarm threshold based on the monitored rate of gas flow in the conduit and the pressure at a patient during the learn period. Thus, the present method can set the alarm threshold to account for the specific condition of the pressure support system, such as the introduction of a supplemental breathing gas, e.g., oxygen, into the system and not produce a false alarm.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 4 is a flow chart illustrating the steps performed in determining the alarm threshold according to the principles of the present invention.

DETAILED DESCRIPTION OF THE INVENTION

Figure 1:
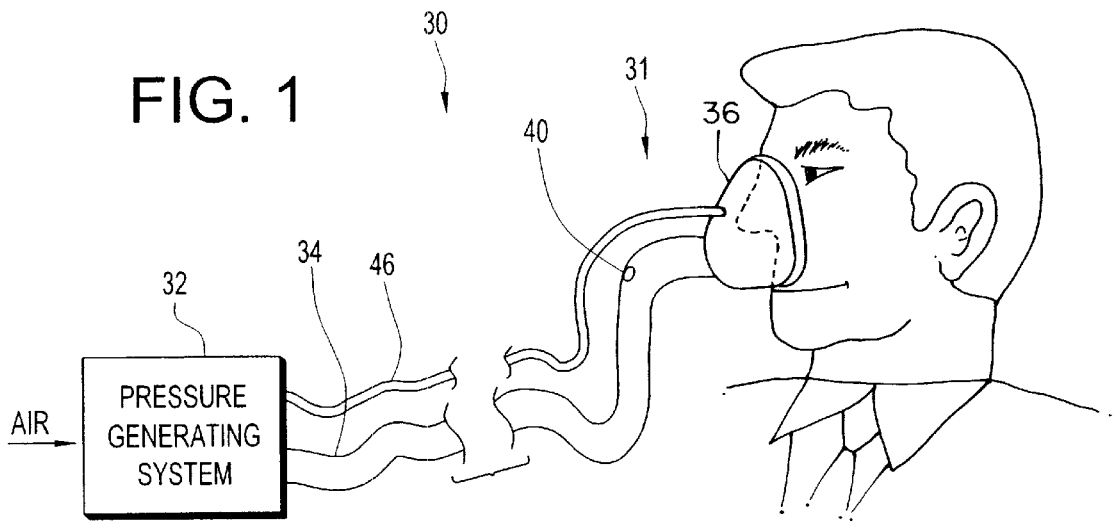
FIG. 1 is schematic diagram of a pressure support system according to the principles of the present invention.

The basic components of a pressure support system 30 according to the principles of the present invention are discussed below with reference to FIGS. 1 and 2. Pressure support system 30 includes a pressure generating system 32 and a patient circuit 31, which includes a conduit 34 and a patient interface 36. Pressure generating system 32 is a ventilation or pressure support device that delivers breathing gas to the patient at a variable or constant pressure that is greater than atmospheric pressure. Pressure generating system 32 includes a pressure generating device 33, such as a blower, bellows or piston, that receives a breathing gas and outputs the breathing gas at a pressure that is greater than atmosphere.

Typically, the breathing gas received by pressure generating device 33 is air taken from the ambient atmosphere. It is to be understood, however, that the present invention contemplates that a source of pressurized breathing gas can be used in combination with the mechanical pressure generating device to provide the breathing gas to the patient at an elevated pressure. For example, in the embodiment illustrated in FIGS. 1 and 2, pressure generator 32 is a mechanical pressure generator, such as a blower, bellows or piston, that receives ambient air at an inlet as the gas source. FIG. 2 further illustrates an optional arrangement in which a supplemental gas, such as oxygen from an oxygen source 35, is delivered to the inlet of the pressure generator via a delivery tube 37.

It is to be further understood that pressure generator 33 can also be a source of pressurized air, oxygen or an oxygen mixture in lieu of a mechanical pressure elevating device. For example, pressurized air can be provided to the airway of the patient directly from a tank of pressurized air via the patient circuit without using a mechanical device, such as a blower, bellows or piston, to increase the pressure of the air. The important feature with respect to the present invention is that pressurized breathing gas is provided in the patient circuit for delivery to the patient, not necessarily the source of the pressurized breathing gas.

If the pressure of the breathing gas delivered to the patient is variable, pressure generating system 32 includes a mechanism that creates the pressure variations. Examples of suitable pressure control mechanisms include (1) a pressure control valve (not shown) downstream of the blower, bellows or piston or (2) a variable speed motor (not shown) associated with the blower, bellows or piston to vary the pressure output by pressure generator 33 by controlling blower, bellows or piston speed. The pressure control valve or viable speed motor typically operate under the control of a control unit 38 in a feedback fashion based on signals from sensors associated with the patient circuit. A pressure support system that provides a variable pressure to the patient based on patient's respiratory cycle, for example, is taught in U.S. Pat. Nos. 5,148,802 and 5,433,193, both to Sanders et al., the contents of which are incorporated by reference into the present application.

Although pressure generating system 32 has been described above in the context of providing CPAP or bilevel pressure therapy to a patient, it is to be understood that other types of pressure support functions can be provided by this system. For example, the present invention contemplates that pressure generating system 32 can correspond to a pressure support device that provides proportional airway pressure ventilation or PAV® to the patient, as taught, for example, in U.S. Pat. No. 5,044,362 to Younes, the contents of which are incorporated by reference into the present application. Pressure generating system 32 can also provide proportional positive airway pressure or PPAP to the patient, as taught, for example, in U.S. Pat. Nos. 5,535,738 and 5,794,615 both to Estes et al., the contents of which are also incorporated by reference into the present application, which teach providing PPAP to treat OSA and to treat congestive heart failure (CHF), respectively. Furthermore, pressure generating system 32 can correspond to a system that monitors the conditions of the patient, such as the occurrence of snoring or an apnea or a lack thereof, and automatically alters the pressure provided to the patient based on this monitoring.

In the illustrated embodiment, conduit 34 has one end coupled to the output of the pressure generator 33 and another end coupled to patient interface 36. Conduit 34 is any tubing capable of carrying the gas flow from the pressure generator to the airway of the patient. Typically, a distal portion of the conduit 34 relative to pressure generator 33 is flexible to allow for freedom of movement of the patient. It is to be understood that various components may be provided in or coupled to patient circuit 31. For example, a bacteria filter, pressure control valve, flow control valve, sensor, meter, pressure filter, humidifier and/or heater can be provided in or attached to the patient circuit.

Patient interface 36 in patient circuit 31 is any device suitable for communicating an end of conduit 34 with the airway of the patient. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive.

In the single limb patient circuit of the present invention, a majority of the exhaled gas from the patient exits the pressure generating system via an exhaust vent 40. In the illustrated embodiment, exhaust vent 40 is provided on a distal portion of conduit 34. Depending on the tidal volume of the patient, a small percentage of the exhaled gas may travel back up the conduit into pressure generator 33 and may even be exhausted to atmosphere through the gas inlet of the pressure generator and/or through a pressure control valve associated therewith, if such a valve is being used with the pressure generator. Typically, exhaust vent 40 is an orifice provided in the conduit that communicates the interior of the conduit with atmosphere, with no active control over the flow of gas from the system. It is to be understood, however, that a wide variety of exhaust devices and configurations are contemplated for use with the pressure generating system of the present invention. For example, U.S. Pat. No. 5,685,296 to Zdrojkowski et al. discloses an exhalation device and method where the exhalation flow rate through the device remains substantially constant over a range of pressures in the patient circuit. This exhalation device, which is commonly referred to as a plateau exhalation valve or PEV, is suitable for use with the pressure support system of the present invention.

Figure 2:
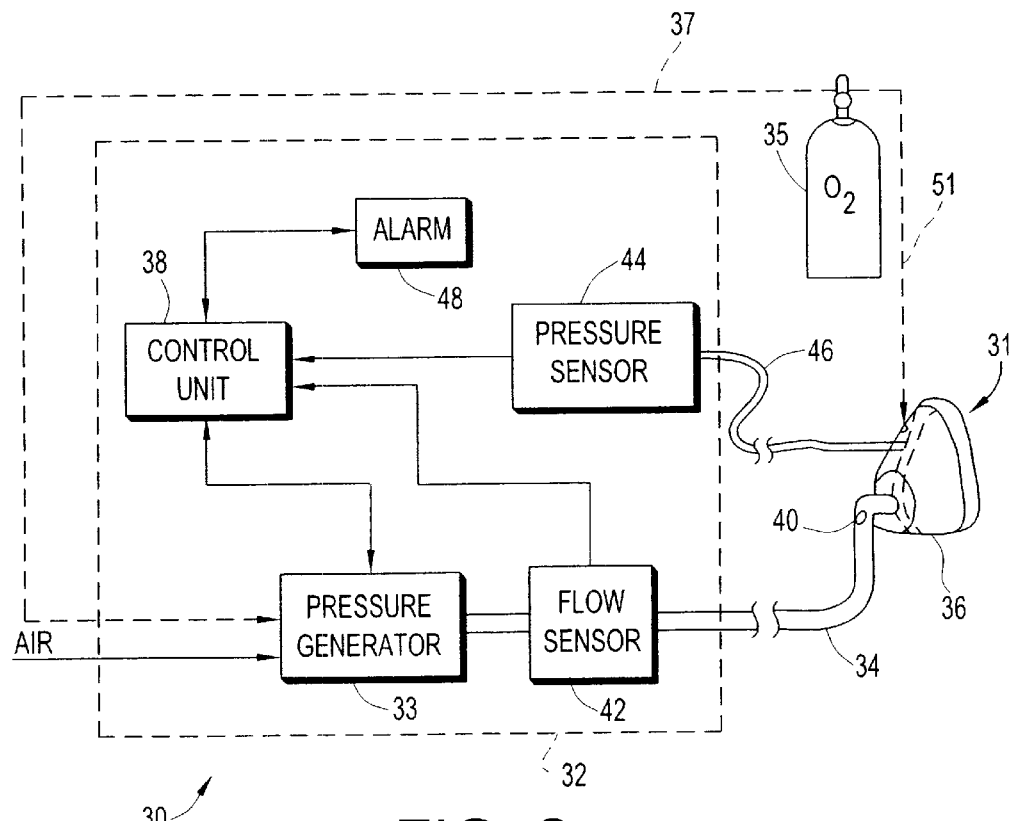
FIG. 2 is a schematic diagram illustrating further details of the pressure support system shown in FIG. 1.

As shown in FIG. 2, pressure generating system 32 in pressure support system 30 also includes a flow sensor 42 that measures a rate at which the breathing gas flows within conduit 34. The present invention contemplates that any suitable sensor, such as a pneumatach, can be used for flow sensor 42. It is to be further understood that flow sensor 42 need not be coupled directly to conduit 34. On the contrary, the present invention contemplates the use of any sensor or a plurality of sensors that can quantitatively measure airflow in the patient circuit. For example, flow in the system can be measured at the patient interface device or can be measured or estimated from the motor or piston speed or from torque used to provide the elevated pressure by pressure generator 33.

Pressure support system 30 also includes a pressure sensor 44 that detects the pressure of the gas at the patient. In the illustrated embodiment, pressure sensor 44 is in fluid communication with patient interface device 36 via a conduit 46. Furthermore, pressure support system 30 includes an alarm 48 that communicates with control unit 38 to output a human perceptible warning, such as an audible sound or a visual light, to wake and/or warn the user or caregiver of an occlusion of exhaust vent 40.

Although not illustrated, the present invention contemplates that pressure generating system 32 includes an input/output interface device, such as a keypad and/or display, for communicating, information, data and/or instructions between the user and control unit 38. Also, computer communications, either hard-wired or wireless, can be provided to allow an external device to communicate with the control unit using conventional communication methods, such as by modem. In addition, the components illustrated in FIG. 2 need not be in hardwired communication with one another as shown and need not be provided in the same housing. On the contrary, the present invention contemplates, for example, that alarm 48, flow sensor 42 and pressure sensor 44 can be provided at locations remote and external to pressure generating system 32 and can communicate with control unit 38 wirelessly or via hardwires. For example, in a clinical or hospital setting, a single control unit can be used to communicate with a plurality of alarms, sensors, and flow/pressure generators. Alternatively, a central base station can be provided that communicates with a plurality of pressure support systems 30 so that a central operator can monitor the operation and alarms for each system.

As discussed in greater detail below, control unit 38 determines, based on the output of flow and pressure sensors 42 and 44, when the rate of exhaust gas passing through exhaust vent 40, i.e., the system leak rate, falls below an acceptable leak rate level and provides the user or caregiver with a warning, via alarm 48, of this condition. A drop in the system leak rate below the alarm threshold level is an indication that the exhaust ports are at least partially occluded and, therefore, are not venting a sufficient amount of expired gas to atmosphere. This low leak alarm alerts the user and caregiver of the potential that the user may be rebreathing expired $CO_2$ and ensures that the patient or caregiver is warned whenever the exhaust ports become blocked so that appropriated remedial action can be taken.

In general, the present invention determines whether the current rate of exhaust is sufficient, i.e., the exhaust ports are not occluded or significantly occluded so as to create a hazard, by comparing the current system leak with an alarm threshold leak rate. If the current system leak rate is less than the alarm threshold for a predetermined time period, the alarms sounds. The alarm is not actuated unless the current system leak rate is less than the alarm threshold for a predetermined time period to account for transient aberrations in the current leak rate.

For example, the predetermined time period during which the current system leak rate must be less than the alarm threshold before the alarm is triggered is selected to be sufficiently long so that the alarm is not actuated if the patient momentarily blocks the exhaust port while adjusting the mask. On the other hand, the time period should not be so long that the user's exposure to rebreathing of expired gasses posses a safety concern. In a preferred embodiment of the present invention, this period is selected to be approximately one minute.

Figure 3:
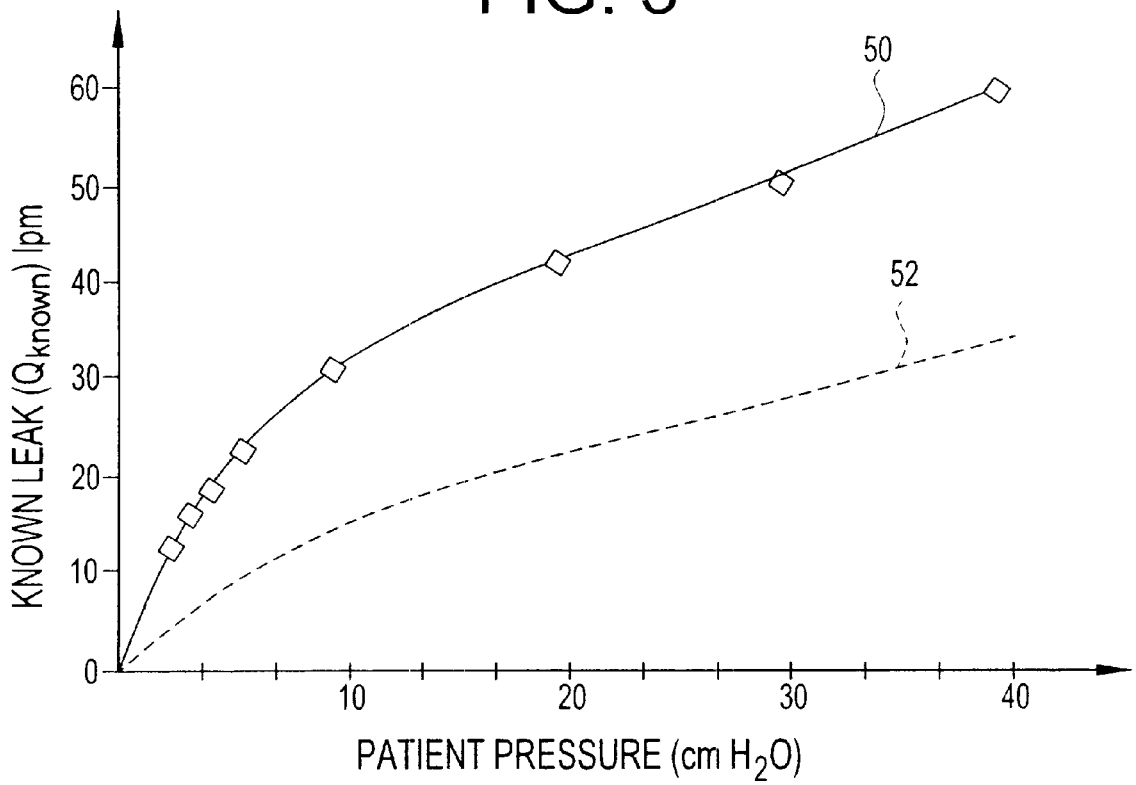
FIG. 3 is a chart illustrating an exemplary relationship between pressure and leak rate for a conventional exhaust port.

In a preferred embodiment of the present invention, operation of the pressure support system begins by having the user perform an exhaust vent test. The exhaust vent test establishes the known rate at which gas flows through the exhaust port, referred to as the known leak rate, $Q_{known}$, over a range of pressures. FIG. 3 illustrates an example of a pressure versus flow relationship 50 between the known leak rate, $Q_{known}$, through a constant orifice exhaust vent over a range of system pressures. It should be noted that different exhaust ports will have different pressure versus flow relationships, because the pressure-flow relationship depends on a number of factors, such as port size and geometry, as well as the density and viscosity of gas passing through the port.

The pressure versus flow relationship determined from the exhaust vent test is used, at least one embodiment, to set the alarm threshold. For example, one embodiment of the present invention contemplates setting the alarm threshold at a certain percentage, such as approximately 50%, less than the known leak. Alternatively, the alarm threshold can be set at a fixed flow rate, such as 5 liters per minute (1 pm), less than the known leak. The pressure versus flow relationship 52 corresponding to an alarm threshold leak rate over a range of pressures that is approximately 50% less than the known leak rate is illustrated in FIG. 3.

By determining the pressure versus flow relationship for the particular system configuration being used by the patient and by basing the alarm threshold on this relationship, the present invention allows the alarm threshold to be optimized for each pressure support system. Thus, the present invention provides flexibility in the alarm generating function to take into consideration that fact that not all pressure supports systems are the same. For example, two pressure support systems may use differently sized exhalation ports so that the rate at which exhaust gas passes through these ports will be different for each system. In which case, different alarm thresholds will be used.

While the present invention is described above as setting the alarm threshold at 50% of $Q_{known}$ or at 5 lpm less than $Q_{known}$, it is to be understood that other alarm thresholds can be selected. The particular percentage of $Q_{known}$ or rate less than $Q_{known}$ will depend, for example, on the patient's tolerance for $CO_2$ rebreathing. For example, in some patients, it may be desirable that as little $CO_2$ rebreathing as possible occurs. In which case, the alarm threshold is set higher than those patients in which a greater amount of $CO_2$ rebreathing is tolerable. It should also be noted that different alarm thresholds can used depending on the whichever one is higher or lower or depending on the monitored conditions. For example, one alarm threshold may be used for patient pressures up to 10 $cmH_2O$, and another threshold used for patient pressures at or above 10 $cmH_2O$.

It should also be noted that the pressure support system being used by one patient may not always have the same configuration or may not be used in the same manner by that patient. In which case, it is again preferable that the same alarm not be used in both configurations or uses. For example, the user may introduce oxygen as a supplemental gas downstream of the flow sensor during a portion of the pressure support therapy or may change the type or number of exhaust ports. A common alarm threshold would not be suitable if either of these alterations in the pressure support system have taken place. Instead, different alarm thresholds should be used for the original system and the modified system. Thus, it is particularly advantageous that the present invention allows the alarm threshold to be optimized for the specific pressure support system being used by the patient.

In a preferred embodiment of the present invention, the exhaust vent test is performed by the user, e.g., the patient or caregiver, once the system configuration is established. For example, once the system has been assembled and is ready for use, an input device, such as a button provided on the housing of pressure generating system 32 or a remote control that communicates with control unit 38, is actuated by the user to initiate the exhaust vent test. To perform the exhaust vent test, the user blocks the end of the patient circuit, for example, by blocking the opening in the mask, so that all gas delivered to the patient circuit is vented to atmosphere through the exhaust vent. The pressure generating system 32 then varies the pressure delivered to the patient circuit and measures the flow in the conduit associated with each pressure level. In a preferred embodiment of the present invention, the system also detects the pressure at patient interface 36 using pressure sensor 44 and measures the flow through conduit 34 at that pressure and plots this pressure-flow relationship, as shown, for example, in FIG. 3. The diamond-shaped boxes in pressure versus flow relationship 50 represent specific pressure-flow points measured in this manner.

Once a number of such points have been determined over a range of pressures, any one of a number of techniques are used to define the pressure versus flow relationship. For example, in a preferred embodiment of the present invention, control unit uses 38 linear interpolation between the fixed, measured points, which are calculated at 10 msec intervals, to derive the pressure versus flow relationship 50, $Q_{known}$, over a range of pressures. As a result of performing the exhaust vent test, the flow out of the exhaust vent, $Q_{known}$, which is also referred to as the leak rate, that is expected for any pressure detected at the patient interface device is known.

As noted above, in normal circumstances, $Q_{known}$, represented by pressure versus flow relationship 50, is used to set the alarm threshold 52. For example, the alarm threshold in one embodiment of the present invention is set at 50% less than $Q_{known}$ or at 5 lpm less than $Q_{known}$. If the total system leak during normal operation falls below this alarm threshold for more than a predetermined period of time, such as one minute, the alarm triggers.

As noted above, this one minute delay is provided to give a modicum of noise immunity in the alarm detection. In the normal case, when the accumulation of the patient's secretions are blocking the exhaust port, there will be a steady decline in the total system leak and reasonable delays, such as one minute, can be used without sacrificing patient safety.

In a preferred embodiment of the present invention, the results of the exhaust vent test are also used to verify the integrity of the exhaust vent and to verify that the exhaust vent test was valid. For example, maximum and/or minimum leak rates can be set so that if these rates are exceeded during the exhaust vent test, this is an indication that the test was performed incorrectly and/or that the exhaust vents are leaking excessively or are occluded. For example, in a preferred embodiment of the present invention, the known leak should less than 80 lpm at 40 $cmH_2O$, otherwise there is deemed to be an excessive leak in the exhaust port and/or the exhaust vent test is considered invalid. Similarly, $Q_{known}$ should be greater than 5 lpm at 20 $cmH_2O$, otherwise there is deemed to be an insufficient leak in the exhaust port and/or the exhaust vent test considered invalid.

It can be appreciated that a wide variety of parameters associated with the pressure versus flow relationship can be monitored to determine the validity of the exhaust vent test. For example, the present invention also contemplates that as the pressure increases, the flow cannot decrease by more than 5 lpm. Monitoring these parameters ensures the accuracy of the exhaust vent test and that the exhaust vents are operating within acceptable parameters.

The present invention also uses the exhaust vent test to test the operation of pressure generating system 32. For example, if pressure generating system 32 is instructed to output a certain pressure, the pressured measured by pressure sensor 44 provides a check on the ability of the pressure generating system to hit the target pressure. In a preferred embodiment of the present invention, the pressure generating system is instructed to output a pressure of 30 cmH$_2$O. If the pressured measured by pressure sensor 44 is ±2 cmH$_2$O from 30 cmH$_2$O, the flow/pressure generating system is considered to be operating normally.

The present invention contemplates that the pressure versus flow relationship, $Q_{known}$, for a particular pressure support system configuration can be established without performing the above-described exhaust vent test. More specifically, the pressure versus flow relationship, i.e., $Q_{known}$, for a plurality of different patient circuits or a plurality of different types of exhaust ports that can be inserted into or used with the patient circuit are stored in advance in control unit 38. The user can designate the patient circuit and/or the exhaust vent that is being used in their particular pressure support system configuration, and the appropriate relationship for that patient circuit and/or exhaust vent is retrieved from memory and used to set the alarm threshold. This embodiment provides the flexibility advantages associated with performing the exhaust vent test but does not require the user to perform this test. It does, however, require that the pressure versus flow relationship for a variety of different exhaust vents or patient circuit be determined in advance and stored in the pressure support system. It also requires that there by a technique for identify the particular type of exhaust vent and/or patient circuit to the control unit so that the appropriate pressure versus flow relationship for that exhaust vent and/or patient circuit can be retrieved. Of course, the pressure versus flow relationship can be manually entered or downloaded to the control unit for each patient circuit and/or exhaust port.

The present invention also contemplates that the control unit automatically retrieve the proper pressure versus flow relationship by identifying which patient circuit and/or exhaust port is currently being used in the pressure support system. Automatically identifying the patient circuit and/or exhaust port being used in the pressure support system can be accomplished, for example, using a resistance identification technique. According to this technique, for example, the control unit can recognize, via an electrical contact on the patient circuit and/or the exhaust vent and an identification resistance located thereon, which patient circuit and/or exhaust vent is coupled to the pressure generating system.

If exhaust vent test is not performed or if the pressure versus flow relationship, i.e., $Q_{known}$, for the exhaust vent patient circuit is not known, the system sets $Q_{known}$ to zero and the alarm threshold is set based on the known flow rate out of the smallest exhaust port that can be used with the patient circuit, referred to as the "minimum exhalation port." For example, in a preferred embodiment of the present invention the alarm threshold is set to 50% or 5 lpm less than the flow rate out of the minimum exhalation port when $Q_{known}$ cannot not be established using either of the other two techniques discussed above.

Of importance in carrying out the present invention is the ability to accurately measure the system leak, i.e., the rate at which gas exits the pressure support system. This is done in the present invention by first assuming that, based on human physiology, over a single breath, a person exhales generally the same amount of gas that he or she inhales so that the patient's end tidal volume is zero. This circumstance most definitely is true over an integral number of breaths, and assuming it to be true over a single breath is a close approximation. Stated another way, the integral of patient flow, $Q_p$, over any one complete breathing cycle is zero, as follows:

$$\int^{T_{breath}} Q_p dt = 0. \qquad (1)$$

Because pressure support system 30 has no provision for measuring the patient flow $Q_p$, the pressure support system of the present invention instead measures the flow, $Q_c$, in the patient circuit, i.e., the flow within conduit 34. Flow in the patient circuit $Q_c$ is measured, for example, by flow sensor 42. The flow in patient circuit $Q_c$ is the sum of the patient flow and any leak flows and is defined as follows:

$$Q_c = Q_p + Q_{leak} \qquad (2)$$

where, $$Q_{leak} = Q_{known} + Q_{unknown} \qquad (3)$$

$Q_{unknown}$ is any leak other than the known leak $Q_{known}$ out of the exhaust port, which, as discussed above, is determined via the exhaust port test or from predetermined pressure versus flow data. $Q_{unknown}$ is modeled according to the following equations:

$$Q_{unknown} = R_{leak} \sqrt{P_p} \qquad (4)$$

if $R_{leak}$ is positive or zero, and $$Q_{unknown} = R_{leak} \qquad (5)$$

if $R_{leak}$ is negative. $P_p$ is the pressure at the mask measured by pressure sensor 44 in FIG. 2, for example. $R_{leak}$ is a constant that is calculated by the processor in control unit 38 and is described in greater detail below.

Determining whether the constant $R_{leak}$ is positive, zero or negative is accomplished by determining whether the following relation is positive, zero or negative:

$$\int^{T_{breath}} (Q_c - Q_{known}) dt \qquad (6)$$

As noted above, $Q_c$ is the measured flow in the patient circuit, preferably measured by flow sensor 42, and $Q_{known}$ is a predetermined known flow out of the exhaust port associated with the measured pressure at the patient interface device. Preferably, the pressure at the patient interface device is measured by pressure sensor 44.

If the result of equation (6) is positive or zero, $R_{leak}$ it is calculated as follows:

$$R_{leak} = \frac{\int^{T_{breath}} (Q_c - Q_{known}) dt}{\int^{T_{breath}} \sqrt{P_p} dt}. \qquad (7)$$

If the result of equation (6) is negative, $R_{leak}$ is calculated as flows:

$$R_{leak} = \frac{\int^{T_{breath}}(Q_c - Q_{known})dt}{T_{breath}} \qquad (8)$$

Once the sign of equation (6) is known, the appropriate equation, i.e., equation (7) or (8), is used to calculate $R_{leak}$, which is then used in either equation (4) or equation (5) for determining $Q_{unknown}$. For example, if equation (6) is positive or zero, equation (7) is used to calculate $R_{leak}$, which is then used in equation (4) for determining $Q_{unknown}$. If, on the other hand, equation (6) is negative, $R_{leak}$ is calculated using equation (8), and used in equation (5) to calculate $Q_{unknown}$. In this manner, the present invention calculates system leak as a function of pressure. It should be noted that equation (6) is the equation used in the numerator of equations (7) and (8) to determine $R_{leak}$. Therefore, the steps to determine the sign of equation (6) are directly applicable to the calculation to determine $R_{leak}$ using equation (7) or (8). Similarly, the sign of $R_{leak}$ is determined based on equation (6) because the denominators of equations (7) and (8) are never negative in a positive pressure support system.

Figure 5:
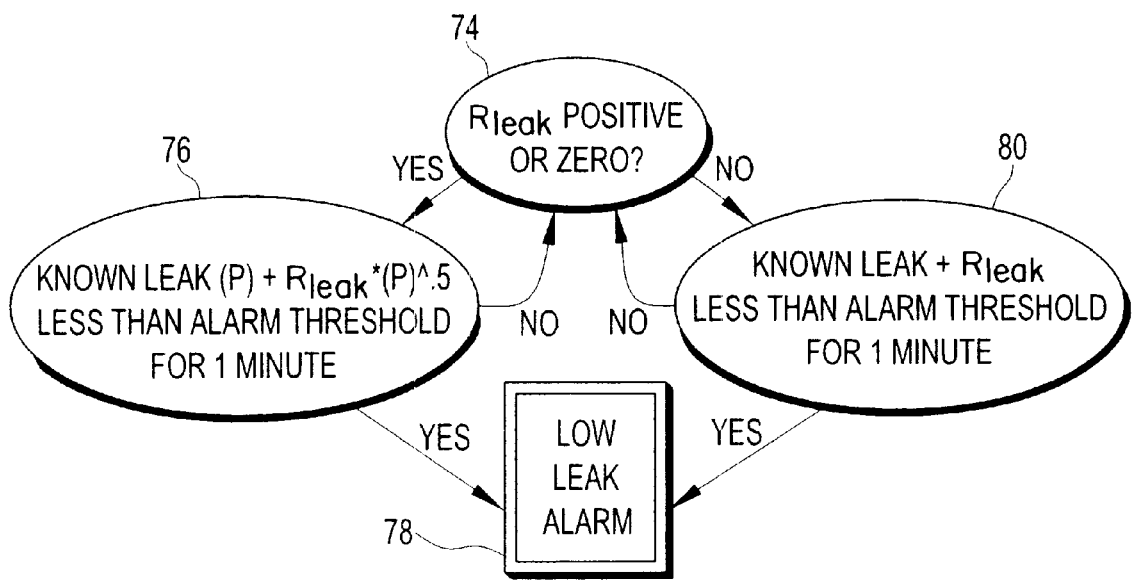
FIG. 5 is a flow chart illustrating the steps performed in monitoring the current system leak and comparing this leak rate to an alarm threshold to determine whether the current system leak through the exhaust port is below an acceptable value.

The operation of the system is described below with reference to FIGS. 4 and 5. FIG. 4 illustrates the process carried out by the pressure support system 30, and, in particular, control unit 38, in establishing the alarm thresholds. FIG. 5 illustrates the process by which the control unit compares the current system leak, which is determined from data gathered from the flow and pressure sensors, with the alarm threshold to determine whether the leak rate from the system is below an acceptable level.

The operation of the pressure support system of the present invention begins by causing the system to enter a learn period, shown in step 54, which is initiated in any one of a variety of ways. In an exemplary embodiment of the present invention, as illustrated in FIG. 4, the learn period in step 54 is initiated either (1) automatically when the system is activated, preferably after a system diagnostic is completed, step 56, (2) when a manual input device, such as a learn key, is actuated, step 58, or (3) automatically after a change in the operating mode of the pressure support system, step 60.

The learn period is a period of time during which a learned constant $R_{leak}$ is calculated and stored in control unit 38. The learned constant $R_{leak}$ is the same constant $R_{leak}$ discussed above except that the learned constant $R_{leak}$ is determined over this learn period. In a preferred embodiment of the present invention, the learn period is a one minute time interval. It is to be understood, however, that the length of the learn period is not limited to this particular value. On the contrary the learn period is any time interval that is long enough to allow the patient to enter their normal breathing pattern. Typically, this takes approximately 1–5 minutes.

During this period, the pressure at the patient interface and the flow in the patient circuit is measured and used by the control unit to calculate equation (6), which, as discussed above, is then used to establish whether equation (7) or (8) is used to calculate the learned constant $R_{leak}$. The appropriate equation (7) or (8) is selected and the learned constant $R_{leak}$ is calculated. If the learned constant $R_{leak}$ at the end of the learn period is positive or zero, no special processing is necessary. If, however, $R_{leak}$ at the end of the learn period is negative, then the system is placed into a special mode of low leak detection discussed in greater detail below.

A negative learned constant $R_{leak}$ at the end of the learn period implies, in most cases, one of two scenarios. The first scenario occurs if the caregiver adds a supplemental gas, such as oxygen, downstream of flow sensor 42 into the patient circuit during the learn period. FIG. 2 illustrates this scenario, with dashed line 51 representing an oxygen delivery tube that delivers oxygen from source 35 to patient interface device 36, which is downstream of flow sensor 42 relative to flow provided by pressure generator 33. Delivering a supplemental gas flow to the patient circuit downstream of flow sensor 42 increases the learned constant $R_{leak}$ negatively because leak flow is modeled above in a direction leaving the circuit, while the supplemental gas, on the other hand, is entering the circuit. If, during the known period, the known leak, $Q_{known}$, out of the exhaust vent is less than the rate at which the supplemental gas is added, the learned constant $R_{leak}$ will be negative. It should be understood that this is possible because leaks at the mask-patient interface, for example, can vent off the excess supplemental gas and/or the excess supplemental gas may back-up into the pressure generator and possibly exit the system from the pressure generator inlet or pressure control valve associated therewith.

The second scenario that can cause the learned constant $R_{leak}$ to be negative at the end of the learn period pertains to the exhaust vent test. If the user performs the exhaust vent test with a given leak device and then switches the exhaust vent with a more restrictive exhaust port that is used to calculate the learned constant $R_{leak}$ during the learn period, the learned constant $R_{leak}$ detected during the learn period will become negative. Similarly, if the learn period is executed with the same exhaust vent used during the exhaust vent test but the exhaust vent is more obstructed during the learn period than it was during the exhaust vent test, it appears to the control unit that a new, more restrictive exhaust vent has replaced the previous exhaust vent and the alarm threshold will be reduced, as discussed below, because the learned constant $R_{leak}$ will be negative. It should be understood that the learned constant $R_{leak}$ is calculated during the learn period based on $Q_{known}$, which is determined, at least in one embodiment, based on the exhaust vent test and in another embodiment based on predetermined pressure versus flow relationships. Therefore, using a different exhaust vent in the exhaust vent test than that used during the learn period, retrieving pressure versus flow information for the wrong patient circuit or exhaust vent, or changing the rate of exhaust between the exhaust vent test and the learn period for the same exhaust vent, such as would occur if the vent becomes obstructed, affects the results of the learn period and can cause the resulting learned constant $R_{leak}$ to be negative.

If the learned constant $R_{leak}$ determined at the end of the learn period is positive or zero, the alarm threshold is determined based on whether or not the exhaust vent test was performed, step 62. If the exhaust vent test was determined to have been performed in step 62, the alarm threshold is set in step 64, according to a preferred embodiment of the present invention, as either (1) a predetermined percentage of the known leak rate, $Q_{known}$, determined during the exhaust vent test or (2) a predetermined amount less than this known exhaust vent leak rate. In a preferred embodiment of the present invention, whichever alarm threshold is the smallest is used. An example of this alarm threshold is illustrated in FIG. 3 by curve 52, which is generally 50% of the known leak 50. In a preferred embodiment of the present invention, and as illustrated in FIG. 4, the alarm threshold is set to either 50% or 5 lpm less than the known leak $Q_{known}$, whichever is smaller.

It is to be understood that different percentages of the known leak, amounts of the known leak or combinations of the two can be used as the alarm threshold depending, for example, on the detected pressure. For example, an alarm threshold of 75% of the known leak can be used for pressures between 0–5 cmH$_2$O and an alarm threshold of 50% of the known leak or 5 lpm less than the known leak, whichever is smaller, can be used for all other pressures.

It is to be understood that the alarm threshold will also be set as described above with respect to step 64 if the known leak, $Q_{known}$, is established based on data stored in memory. The effect of (1) performing the exhaust vent test or (2) recalling predetermined pressure versus flow data from memory based on the system configuration, and, more particularly, the type of exhaust vent or vents used, is the same. In both situations, a known pressure versus flow relationship, $Q_{known}$, is established so that the flow out of the exhaust vent associated with a given pressure at the patient interface device is known.

If the exhalation vent test was not performed or if the pressure versus flow relationship is not known, the alarm threshold is set in step 66 as either (1) a predetermined percentage or (2) a predetermined amount less than the leak from the smallest known port that can be used in the patient circuit. Preferably, whichever of the predetermined percentage or the predetermined amount less than the leak from the smallest known port that results in the lowest alarm threshold is used. Also, in this situation, the known leak, $Q_{known}$, is set to zero in step 68.

If the learned constant $R_{leak}$ at the end of the learn period is negative, the alarm threshold must be carefully monitored to ensure that false alarms are not generated, which might otherwise occur, for example, once the caregiver ceases supplying supplemental oxygen. If the learned constant $R_{leak}$ at the end of the learn period is negative, the alarm threshold is set in step 70 as the sum of the known leak, $Q_{known}$, and the constant $R_{leak}$, which was determined in the learn period, minus either (1) a predetermined percentage of the sum of the known leak, $Q_{known}$, and the constant $R_{leak}$ or (2) a predetermined amount of flow less that this sum. In the exemplary embodiment illustrated in FIG. 4, the alarm threshold is set in step 70 as either 50% or 5 lpm less than the known leak, $Q_{known}$, plus the constant $R_{leak}$ established as a result of the learn period. The known leak value $Q_{known}$ varies with pressure, but the learned constant $R_{leak}$ established as a result of the learn period is now representative of an average leak valve and does not change with pressure.

Setting the alarm threshold in the manner discussed above with respect to step 70 is necessary to prevent situations, for example, where supplemental oxygen is added to the patient circuit downstream of the pressure/flow generator from generating a false alarm. When the supplemental gas is first introduced, the user initiates the learn period, for example, by actuating the learn key. (It is also preferable for the user to make sure that the patient interface device is properly positioned.) The system sets the alarm threshold as discussed above taking into consideration the fact that supplemental gas is being introduced into the patient circuit.

When the supplemental gas is not longer being administered, the system leak will return to its original value. Therefore, it is preferable to again initiate the learn period in step 54 to reestablish the normal baseline alarm threshold of the exhaust port without the supplemental gas being introduced into the system. Preferably, the user actuates the learn key, step 58, to initiate the learn period. However, the present invention contemplates that the learn period can be automatically. For example, if the system detects that a new exhaust port has replaced the previous port, the learn period can be automatically entered.

If, however, the learn period is not initiated at the cessation of the supplemental gas therapy, either manually or automatically, the system of the present invention automatically returns the alarm threshold to the exhaust port's baseline values. This is accomplished in step 72 in FIG. 4. According to step 72, if the learned constant $R_{leak}$ was determined to be negative during the learn period, the system continuously calculates $R_{leak}$. If $R_{leak}$ becomes zero or positive for a predetermined period of time, such as one (1) minute, the alarm threshold is then set as discussed above according to step 64 or step 66 depending on whether the exhaust vent test was performed (step 62). Otherwise, if $R_{leak}$ remains negative, the alarm threshold continues to be set according to step 70. It is to be understood that the predetermined period of time set forth in step 72 can be values other than one minute, so long as this period of time is sufficient to detect an actual change in the system configuration and not a temporary phenomena, such as a readjustment of the patient interface device by the user.

The present invention further contemplates that the alarm threshold can be altered automatically (without waiting for $R_{leak}$ to be positive for a predetermined period of time as required by step 72) based on detected changes in the pressure support system. For example, sensors or other means can be provided for determining when the supplemental gas is no longer being introduced into the system. For example, a valve controlling the supplemental gas supply, or a control unit that controls the valve, can signal when the valve is shut, thereby causing the system to move from step 70 to step 62. Alternatively, an oxygen sensor, for example, can be provided to detect when oxygen is no longer being administered to the patient and cause the system to enter the reset the alarm threshold via steps 62–66.

This automatic resetting of the alarm threshold also guards against users that mistakenly initiate the learn period when no exhaust port is present in the patient circuit or when the exhaust port is blocked. In these situations, the learned constant $R_{leak}$ will likely be calculated during the learn period as being negative. If the exhaust port is later added to the circuit, becomes unblocked, or if another leak occurs, such as leak at the mask seal, $R_{leak}$ becomes positive. This is detected in step 72, and the alarm threshold is set according to steps 64 or 66. Thus, the pressure support system of the present invention automatically corrects the alarm threshold for such user errors and other events to prevent false alarms.

FIG. 5 illustrates the steps the control unit performs in determining whether the system leak through the exhaust port is below an acceptable value during normal operation of the pressure support system after the alarm threshold has been set as discussed above with respect to FIG. 4. During operation, the pressure support system continuously determines in step 74 whether the constant $R_{leak}$ is positive or not. This is accomplished by continuously calculating equation (6) based on the pressure and flow measurements discussed above. (See above). Only equation (6) need be considered because equation (6) is the numerator for both equations (7) and (8). The denominator for these equations is never negative. Thus, the result of calculating equation (6) establishes whether $R_{leak}$ is positive, zero or negative.

If the result of equation (6) is positive or zero, the system compares in step 76 the sum of the known leak, $Q_{known}$, and $R_{leak}*\sqrt{P_p}$ to the alarm threshold established as discussed above with respect to FIG. 4. It should be noted that the product $R_{leak}*\sqrt{P_p}$, when $R_{leak}$ is positive or zero, corresponds to equation (4) which defines $Q_{unknown}$. Thus, the sum of the known leak, $Q_{known}$, and $R_{leak}*\sqrt{P_p}$, when $R_{leak}$ is positive or zero, corresponds to equation (3) which defines the system leak as $Q_{known}+Q_{known}$, $Q_{known}$. If this sum, i.e. $Q_{leak}$ or system leak, is less than the alarm threshold for more than a predetermined period of time, the low leak alarm is actuated in step 78.

In the illustrated exemplary embodiment, the predetermined period of time is selected to be one (1) minute. It is to be understood that this time period can be other values so long as the period of time is long enough to prevent transient aberrations from causing a false alarm yet not so long that the user suffers from having the system running with the exhaust port completely or partially blocked.

If the result of equation (6) is not positive or zero, i.e. negative, the system compares, in step 80, the sum of the known leak, $Q_{known}$, and $R_{leak}$ to the alarm threshold established, as discussed above, with respect to FIG. 4. It should be noted that when result of equation (6) is negative, $R_{leak}$ corresponds to $Q_{known}$ as set forth above in equation (5). Thus, the sum of the known leak, $Q_{known}$, and $R_{leak}$, when $R_{leak}$ is negative, also corresponds to equation (3), which defines the system leak as $Q_{known}+Q_{unknown}$. If this sum, i.e. $Q_{leak}$ or system leak, is less than the alarm threshold for more than a predetermined period of time, the low leak alarm is actuated in step 78.

A more thorough understanding of the present invention may be appreciated by considering the following examples. It is to be understood that these are hypothetical examples that illustrate, with reference to FIGS. 4 and 5, how the system determines the alarm threshold and uses this threshold to judge whether the system leak rate is below acceptable levels. The values for the leak rate used in these examples are selected to illustrate the system operation and do not necessarily reflect actual values.

EXAMPLE 1

In this example, the pressure support system is as shown in FIG. 1, and no supplemental gas is being delivered to the patient. Suppose that an exhaust vent test has been performed and the known leak rate has been determined to be a constant 30 lpm, $Q_{known}$=30 lpm, for the entire range of operating pressures. Suppose, also, that the learn period has been performed and the learned constant $R_{leak}$ is determined to be positive or zero. The system determines the alarm threshold according to step 64 as, for example, 50% less than $Q_{known}$, i.e., 50% less than 30 lpm or 15 lpm.

After the learn period, the system then continuously determines whether the sign on the constant $R_{leak}$ is positive or zero in step 74 of FIG. 5. As long as $R_{leak}$ remains positive or zero, step 76, which is the test used if $R_{leak}$ is positive, will not produce an alarm because the known leak, $Q_{known}$, plus a positive $R_{leak}$ value multiplied by the square root of pressure at the patient interface, i.e., step 76, will not yield a result that is less than the alarm threshold.

However, as the exhaust vent becomes occluded, $R_{leak}$ will decrease and become negative. If, for example, $R_{leak}$ is −10 lpm, the system leak $Q_{leak}$ will be $Q_{known}+R_{leak}$, see equations (2) and (4) and step 80 in FIG. 5. In this example, $Q_{leak}$=30 lpm+(−10 lpm)=20 lpm. Because 20 lpm is not less than the alarm threshold of 15 lpm, the low leak alarm will not yet be activated. As the exhaust vent becomes more occluded, $R_{leak}$ continues to decrease, i.e., become more negative, and eventually the system leak $Q_{leak}$ will fall below the alarm threshold, and the low leak alarm will sound.

EXAMPLE 2

This example is the same as the pervious example except that the exhaust vent test has not been performed. In this situation, because the learned constant $R_{leak}$ determined during the learn period is positive and because the exhaust vent test was not performed, the alarm threshold is set according to step 66 in FIG. 4, for example, as 50% less than the leak from the minimum exhaust vent that can be used with the patient circuit. Suppose, in this example, that the leak rate from the smallest useable exhaust port is a constant 10 lpm over the range of operating pressures. Half of this rate is 5 lpm, so that the alarm threshold is set at 5 lpm. In addition, $Q_{known}$ is set at zero in step 68.

$R_{leak}$ is continuously calculated in step 74 following the learn period. If, for example, $R_{leak}$ is determined to be 10, the system leak (known leak, $Q_{known}+R_{leak}*\sqrt{P_p}$) in step 76 is determined as follows: $0+10\sqrt{P_p}$ or simply, $10\sqrt{P_p}$; recall that the known leak, $Q_{known}$, was set to zero. It can be appreciated that it may be possible for the value of $R_{leak}$ to decrease, as the exhaust vent becomes occluded, such that $R_{leak}$ drops to a level in which the system leak, $Q_{leak}$ (known leak, $Q_{known}+R_{leak}*\sqrt{P_p}$) falls below the alarm threshold level so that the lower leak alarm sounds. If $R_{leak}$ becomes negative, which might occur if supplemental gas is added to the system, the alarm threshold test set forth in step 80 of FIG. 5 is used. It can be appreciated that as $R_{leak}$ falls as a result of the exhaust vent becoming more occluded, eventually $R_{leak}$ will fall to a level below the alarm threshold and the low level alarm will be actuated.

EXAMPLE 3

This example is the same as Example 1 in that the exhaust vent test has been performed so that $Q_{known}$, i.e., the pressure versus flow relationship for the pressure support system being used by the patient, is established as, for example, 30 lpm over the range of operating pressures. In this example, however, suppose that as a result of the learn period, the learned constant $R_{leak}$ is determined to be negative, such as −10 lpm. The alarm threshold is then set according to step 70 in FIG. 4 as, for example, 50% less than $Q_{known}+R_{leak}$. In this example, $Q_{known}$=30 lpm and $R_{leak}$=−10 lpm so that the alarm threshold is 50% less than 20 lpm or 10 lpm.

Referring now to FIG. 5, the system continuously determines $R_{leak}$ in step 74. If $R_{leak}$ continues to be −10 the system leak, alarm threshold test set forth in step 80 is used because $R_{leak}$ is negative. In step 80, the current system leak, $Q_{leak}$, is $Q_{known}$ (30 lpm)+$R_{leak}$ (−10 lpm)=20 lpm, which is not less than the alarm threshold of 10 lpm so that the alarm is not actuated. As the exhaust port becomes occluded, $R_{leak}$ drops. Eventually, $R_{leak}$ will drop to a level where the system leak, $Q_{known}+R_{leak}$ of step 80, is less than the alarm threshold.

EXAMPLE 4

This example is the same as Example 2 in that the exhaust vent test has not been performed. In addition, at a result of the learn period the learned constant $R_{leak}$ is determined to be negative, for example −10. In this example, as with Example 3, the alarm threshold is set according step 70 in FIG. 4. For example, the alarm threshold is set as 50% less than $Q_{known}+R_{leak}$. In this example, $Q_{known}$=0 lpm and $R_{leak}$=−10 lpm so that the alarm threshold is 50% less than −10 lpm or −15 lpm.

Thereafter, the pressure support system continuously determines $R_{leak}$ in step 74 of FIG. 5. If $R_{leak}$ continues to be negative, the alarm threshold test set forth in step 80 is used. According to step 80, the current system leak, $Q_{leak}$, is determined as $Q_{known}$ (0 lpm)+$R_{leak}$ (−10 lpm)=−10 lpm, which is not less than the alarm threshold of −15 lpm so that the alarm is not actuated. As the exhaust port becomes occluded, $R_{leak}$ drops. Eventually, $R_{leak}$ will drop to a level where the system leak, $Q_{known}+R_{leak}$ because $R_{leak}$ is negative, is less than the alarm threshold.

It should be noted that in Examples 3 and 4, if $R_{leak}$ becomes positive for more than one minute, for example, the alarm threshold will be recalculated as discussed above with respect to step 72 of FIG. 4.

It can thus be appreciated that the pressure support system of the present invention provides an alarm that indicates situations where the system leak rate is below an acceptable level that is reliable for detecting blockage of an exhalation port under a variety of different scenarios. The low leak alarm system of the present invention is particularly advantageous in that the alarm threshold is adaptable to the specific exhaust port requirements through the use of the exhaust vent test or the ability to recall predetermined flow versus pressure relationships for a particular type of exhaust port. Furthermore, the low leak alarm system can detect blockage of the exhaust vent even if a supplemental gas is added to the system while minimizing false alarms once the supplemental gas flow ceases.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A pressure support system comprising:
   a pressure generator adapted to provide a gas flow;
   a conduit operatively coupled to said pressure generator to deliver a gas flow to a patient;
   an interface device operatively coupled to said conduit to communicate a gas flow to an airway of a patient, wherein at least one of said conduit and said interface device includes an exhaust vent that provides a flow of exhaust gas to atmosphere from a respective one of said conduit and said interface device;
   flow sensing means for determining a rate at which gas flows in said conduit and for providing flow signal indicative thereof;
   pressure sensing means for determining a pressure of gas at a patient and for providing a pressure signal indicative thereof; and
   processing means, receiving said flow signal and said pressure signal, for determining whether a current flow of exhaust gas passing through said exhaust vent is below an alarm threshold based on said flow signal and said pressure signal and for providing an output indicative of said determination.

2. A pressure support system according to claim 1, further comprising an alarm device operatively coupled to said processing means to receive said output, wherein said processing means generates said output responsive to said current flow of exhaust gas being below such an alarm threshold for a predetermined period of time, and wherein said alarm device outputs a human perceivable alarm responsive to receiving said output.

3. A pressure support system according to claim 1, wherein said processing means sets said alarm threshold according to at least one detected condition of said pressure support system determined during a learn period, wherein said learn period is a period of time in which at least one parameter associated with said pressure support system is monitored by said processing means using at least one of said flow sensing means and said pressure sensing means.

4. A pressure support system according to claim 3, further comprising a manual input device operatively coupled to said processing means, wherein said pressure support system is capable of being operated in a plurality of modes, and wherein at least one of (1) actuation of said manual input device, (2) start up of said pressure support system, and (3) a change in a mode of operation of said pressure support system causes said processing means to execute said learn period.

5. A pressure support system according to claim 3, wherein said detected conditions include said rate at which gas flows in said conduit and said pressure of gas at a patient, and wherein said processing means (1) determines a first relationship defined as:

$$\int^{T_{breath}} (Q_c - Q_{known}) dt$$

during said learn period, where $Q_c$ is a current flow of gas within said conduit, $Q_{known}$ is a predetermined flow of exhaust gas passing through said exhaust vent, and $T_{breath}$ is an integral number of breathing cycles, and (2) sets said alarm threshold based on a first set of criteria responsive to said first relationship being negative and based on a second set of criteria responsive to said first relationship not being negative.

6. A pressure support system according to claim 5, wherein said processing means calculates a second relationship, $R_{leak}$, defined as:

$$R_{leak} = \frac{\int^{T_{breath}} (Q_c - Q_{known}) dt}{T_{breath}},$$

and wherein said processing means sets said alarm threshold as one of (1) a predetermined percentage less than a sum of $Q_{known}$, and $R_{leak}$ and (2) a predetermined amount less than a sum of $Q_{known}$, and $R_{leak}$, responsive to said first relationship determined during said learn period being negative.

7. A pressure support system according to claim 5, wherein said processing means also monitors said first relationship during nominal operation of said pressure support system and changes from said first set of criteria to said second set of criteria by which said alarm threshold is set responsive to said first relationship not being negative for a predetermined period of time and thereafter adjusts said alarm threshold according to said second set of criteria.

8. A pressure support system according to claim 5, wherein $Q_{known}$ is determined by one of:
   (1) performing an exhaust vent test that includes:
      (a) providing a plurality of pressures to a patient via said pressure generator,
      (b) measuring a current flow of gas within said conduit associated with each of said plurality of pressures,
      (c) establishing a pressure versus flow relationship for said exhaust vent based on said plurality of pressures and flow associated therewith, and
      (d) setting $Q_{known}$ based on said pressure versus flow relationship;
   (2) recalling $Q_{known}$ from a database based on said exhaust vent being used with said pressure support system, wherein said data base contains a plurality of pressure verses flow relationships associated with various types of exhaust vents; and
   (3) setting $Q_{known}$ to zero if both steps (1) and (2) are not performed.

9. A pressure support system according to claim 8, wherein said processing means sets said alarm threshold as one of (1) a predetermined percentage of $Q_{known}$ and (2) a predetermined amount less than $Q_{known}$, responsive to said first relationship determined during said learn period not being negative and one of (1) said exhaust vent test having been performed and (2) $Q_{known}$ having been recalled from said database, and wherein said processing means sets said alarm threshold as one of (1) a predetermined percentage of a predetermined minimum exhaust vent leakage rate and (2) a predetermined amount less than said predetermined minimum exhaust vent leakage rate responsive to said first relationship determined during said learn period not being negative and said exhaust vent test and recalling of $Q_{known}$ from said database having not been performed.

10. A pressure support system according to claim 9, wherein said processing means determines, during normal operation of said pressure support system, whether a current flow of exhaust gas passing through said exhaust vent is below said alarm threshold by repeatedly determining whether said first relationship is negative, and wherein said processing means calculates, during normal operation, a constant $R_{leak}$ according to a second relationship defined as:

$$R_{leak} = \frac{\int^{T_{breath}}(Q_c - Q_{known})dt}{\int^{T_{breath}}\sqrt{P_p}\,dt}$$

if said first relationship is not negative, wherein $P_p$ is a pressure at an airway of a patient, and according to a third relationship defined as:

$$R_{leak} = \frac{\int^{T_{breath}}(Q_c - Q_{known})dt}{T_{breath}}$$

if said first relationship is negative, and wherein said processing means, during normal operation, provides said third output based on whether a fourth relationship defined as $Q_{known}+R_{leak}\sqrt{P_p}$ is less than said alarm threshold for a first predetermined period of time, responsive to $R_{leak}$ not being negative, and wherein said processing means provides said third output based on whether a fifth relationship defined as $Q_{known}+R_{leak}$ is less than said alarm threshold for a second predetermined period of time, responsive to $R_{leak}$ being negative.

11. A pressure support system according to claim 1, wherein said processing means determines, during normal operation of said pressure support system, whether a current flow of exhaust gas passing through said exhaust vent is below said alarm threshold by repeatedly determining whether a first relationship defined as:

$$\int^{T_{breath}}(Q_c - Q_{known})dt$$

is negative, where $Q_c$ is a flow of gas within said conduit, $Q_{known}$ is a predetermined rate of flow of exhaust gas passing through said exhaust vent, and $T_{breath}$ is an integral number of breathing cycles.

12. A pressure support system according to claim 11, wherein said processing means determines whether said current rate of flow of exhaust gas passing through said exhaust vent is below said alarm threshold by calculating a constant $R_{leak}$ according to a second relationship defined as:

$$R_{leak} = \frac{\int^{T_{breath}}(Q_c - Q_{known})dt}{\int^{T_{breath}}\sqrt{P_p}\,dt}$$

if said first relationship is not negative, wherein $P_p$ is a pressure at an airway of a patient, and according to a third relationship defined as:

$$R_{leak} = \frac{\int^{T_{breath}}(Q_c - Q_{known})dt}{T_{breath}}$$

if said first relationship is negative.

13. A pressure support system according to claim 12, wherein said processing means, during normal operation, provides said third output based on whether a fourth relationship defined as $Q_{known}+R_{leak}\sqrt{P_p}$ is less than said alarm threshold for a first predetermined period of time, responsive to $R_{leak}$ not being negative, and wherein said processing means provides said third output based on whether a fifth relationship defined as $Q_{known}+R_{leak}$ is less than said alarm threshold for a second predetermined period of time, responsive to $R_{leak}$ being negative.

14. A method of providing pressure support including a low leak alarm comprising the steps of:

providing a gas flow from a pressure generator to a patient via a conduit operatively coupled to said pressure generator, wherein an interface device is also coupled to said conduit to communicate a gas flow from said conduit to an airway of a patient, and wherein an exhaust vent in disposed in one of said interface device and a portion of said conduit proximate to said interface device to communicate a flow of exhaust gas to atmosphere from a respective one of said conduit and said interface device;

detecting a rate at which gas flows in said conduit and providing a first output indicative thereof;

detecting a pressure of gas at a patient and providing a second output indicative thereof;

determining whether a current flow of exhaust gas passing through said exhaust vent is below an alarm threshold based on said first output and said second output; and providing a third output indicative of a result of said determining step.

15. A method according to claim 14, further comprising a step of outputting a human perceivable alarm responsive to said current flow of said exhaust gas being below such an alarm threshold for a predetermined period of time.

16. A method according to claim 14, further comprising the steps of:

monitoring said rate at which gas flows in said conduit and said pressure of gas at a patient during a learn period; and setting said alarm threshold based on said monitored gas flow in said conduit and said pressure of gas at a patient during said learn period.

17. A method according to claim 16, wherein said monitoring step includes determining a first relationship defined as:

$$\int^{T_{breath}}(Q_c - Q_{known})dt$$

during said learn period, where $Q_c$ is a current flow of gas within said conduit, $Q_{known}$ is a predetermined flow of exhaust gas passing through said exhaust vent, and $T_{breath}$ is an integral number of breathing cycles; and wherein said alarm threshold setting step includes setting said alarm threshold based on a first set of criteria responsive to said first relationship being negative and setting said alarm threshold based on a second set of criteria responsive to said first relationship not being negative.

18. A method according to claim 17, further comprising a step of calculating a second relationship, $R_{leak}$, defined as:

$$R_{leak} = \frac{\int^{T_{breath}}(Q_c - Q_{known})dt}{T_{breath}},$$

and wherein said setting step includes setting said alarm threshold as one of (1) a predetermined percentage less than a sum of $Q_{known}$, and $R_{leak}$ and (2) a predetermined amount less than a sum of $Q_{known}$, and $R_{leak}$, responsive to said first relationship determined during said learn period being negative.

19. A method according to claim 17, further comprising the steps of:
monitoring said first relationship during normal operation of said pressure support system;
changing from said first set of criteria to said second set of criteria by which said alarm threshold is set responsive to said first relationship not being negative for a predetermined period of time; and
adjusting said alarm threshold based on said second set of criteria.

20. A method according to claim 17, further comprising the step of determining $Q_{known}$ by performing the following steps:
(1) performing an exhaust vent test by performing the following steps:
   (a) providing a plurality of pressures to a patient via said pressure generator,
   (b) measuring a current flow of gas within said conduit associated with each of said plurality of pressures,
   (c) establishing a pressure versus flow relationship for said exhaust vent based on said plurality of pressures and rates of flow associated therewith, and
   (d) setting $Q_{known}$ based on said pressure versus flow relationship;
(2) recalling $Q_{known}$ from a database based on said exhaust vent being used with said pressure support system, wherein said database contains a plurality of pressure verses flow relationships associated with various types of exhaust vents; and
(3) setting $Q_{known}$ to zero if both steps (1) and (2) are not performed.

21. A method according to claim 20, wherein said alarm threshold setting step includes setting said alarm threshold as one of (1) a predetermined percentage of $Q_{known}$ and (2) a predetermined amount less than $Q_{known}$, responsive to said first relationship determined during said learn period not being negative and one of (1) said exhaust vent test having been performed and (2) $Q_{known}$ having been recalled from said database, and wherein said alarm threshold is set as one of (1) a predetermined percentage of a predetermined minimum exhaust vent leakage rate and (2) a predetermined amount less than said predetermined minimum exhaust vent leakage rate responsive to said first relationship determined during said learn period not being negative and said exhaust vent test and recalling $Q_{known}$ from said database having not been performed.

22. A method according to claim 21, wherein said determining step includes determining, during normal operation, whether a current rate of flow of exhaust gas passing through said exhaust vent is below said alarm threshold by repeatedly determining whether a first relationship defined as:

$$\int^{T_{breath}}(Q_c - Q_{known})dt$$

is negative, where $Q_c$ is a flow of gas within said conduit, $Q_{known}$ is a predetermined flow of exhaust gas passing through said exhaust vent, and $T_{breath}$ is an integral number of breathing cycles, further comprising:

calculating a constant $R_{leak}$ according to a second relationship defined as:

$$R_{leak} = \frac{\int^{T_{breath}}(Q_c - Q_{known})dt}{\int^{T_{breath}}\sqrt{P_p}\,dt}$$

if said first relationship is not negative, wherein $P_p$ is a pressure at an airway of a patient; and calculating a constant $R_{leak}$ according to a third relationship defined as:

$$R_{leak} = \frac{\int^{T_{breath}}(Q_c - Q_{known})dt}{T_{breath}}$$

if said first relationship is negative;

outputting a low leak alarm responsive to a fourth relationship defined as $Q_{known}+R_{leak}\sqrt{P_p}$ being less than said alarm threshold for a first predetermined period of time, responsive to $R_{leak}$ not being negative; and outputting a low leak alarm responsive to a fifth relationship defined as $Q_{known}+R_{leak}$ being less than said alarm threshold for a second predetermined period of time, responsive to $R_{leak}$ being negative.

23. A method according to claim 14, wherein said determining step includes determining, during normal operation, whether a current flow of exhaust gas passing through said exhaust vent is below said alarm threshold by repeatedly determining whether a first relationship defined as:

$$\int^{T_{breath}}(Q_c - Q_{known})dt$$

is negative, where $Q_c$ is a flow of gas within said conduit, $Q_{known}$ is a predetermined rate of flow of exhaust gas passing through said exhaust vent, and $T_{breath}$ is an integral number of breathing cycles.

24. A method according to claim 23, further comprising the steps of calculating a system constant $R_{leak}$ according to a second relationship defined as:

$$R_{leak} = \frac{\int^{T_{breath}}(Q_c - Q_{known})dt}{\int^{T_{breath}}\sqrt{P_p}\,dt}$$

if said first relationship is not negative, wherein $P_p$ is a pressure at an airway of a patient; and calculating a system constant $R_{leak}$ according to a third relationship defined as:

$$R_{leak} = \frac{\int^{T_{breath}}(Q_c - Q_{known})dt}{T_{breath}}$$

if said first relationship is negative.

25. A method according to claim 24, further comprising the steps of:

determining whether $R_{leak}$ not being positive;

outputting a low leak alarm responsive to a fourth relationship defined as $Q_{known}+R_{leak}\sqrt{P_p}$ being less than said alarm threshold for a first predetermined period of time, responsive to $R_{leak}$ not being negative; and outputting a low leak alarm responsive to a fifth relationship defined as $Q_{known}+R_{leak}$ being less than said alarm threshold for a second predetermined period of time, responsive to $R_{leak}$ being negative.

* * * * *